United States Patent
DiMaio et al.

(10) Patent No.: US 12,318,164 B2
(45) Date of Patent: Jun. 3, 2025

(54) SYSTEMS AND METHODS FOR CONTROLLING A ROBOTIC MANIPULATOR OR ASSOCIATED TOOL

(71) Applicant: Intuitive Surgical Operations, Inc., Sunnyvale, CA (US)

(72) Inventors: Simon P. DiMaio, San Carlos, CA (US); Mark Froggatt, Blacksburg, VA (US); Xingchi He, San Jose, CA (US); Govinda Payyavula, Sunnyvale, CA (US); David W. Robinson, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 961 days.

(21) Appl. No.: 17/265,051

(22) PCT Filed: Jul. 29, 2019

(86) PCT No.: PCT/US2019/043857
§ 371 (c)(1),
(2) Date: Feb. 1, 2021

(87) PCT Pub. No.: WO2020/028216
PCT Pub. Date: Feb. 6, 2020

(65) Prior Publication Data
US 2021/0338354 A1    Nov. 4, 2021

Related U.S. Application Data

(60) Provisional application No. 62/713,297, filed on Aug. 1, 2018.

(51) Int. Cl.
*A61B 34/00* (2016.01)
*A61B 34/20* (2016.01)
(Continued)

(52) U.S. Cl.
CPC .............. *A61B 34/74* (2016.02); *A61B 34/20* (2016.02); *A61B 34/35* (2016.02); *A61B 2034/2061* (2016.02); *A61B 2034/302* (2016.02)

(58) Field of Classification Search
CPC ......... A61B 34/74; A61B 34/20; A61B 34/35; A61B 2034/2061; A61B 2034/302;
(Continued)

(56) References Cited

U.S. PATENT DOCUMENTS 8,116,601 B2    2/2012    Prisco et al.
2009/0054733 A1*    2/2009    Marescaux ............ A61B 17/29
600/149

(Continued)

FOREIGN PATENT DOCUMENTS

WO    WO-2011057260 A2    5/2011
WO    WO-2016149320 A1    9/2016
WO    WO-2017098348 A1    6/2017

OTHER PUBLICATIONS

International Search Report and Written Opinion for Application No. PCT/US2019/043857, mailed on Jan. 16, 2020, 17 pages.

(Continued)

*Primary Examiner* — Rami R Okasha
(74) *Attorney, Agent, or Firm* — Haynes & Boone, LLP

(57) ABSTRACT

A system includes a tool, an input device, a shape sensor system, and a processing unit. The processing unit is configured to determine a state estimate of the input device based on shape information from the shape sensor system, and control the tool based on the state estimate.

18 Claims, 10 Drawing Sheets

(51) Int. Cl.
*A61B 34/30* (2016.01)
*A61B 34/35* (2016.01)

(58) Field of Classification Search
CPC .......... G05B 2219/35464; G05B 2219/40279;
G05B 2219/37278; B25J 19/025; B25J
3/04; B25J 9/1694; B25J 13/02; B25J
9/1689
See application file for complete search history.

(56) References Cited

U.S. PATENT DOCUMENTS

| | | | |
|---|---|---|---|
| 2009/0324161 A1 | 12/2009 | Prisco | |
| 2011/0118752 A1* | 5/2011 | Itkowitz | A61B 34/30 345/157 |
| 2011/0319910 A1* | 12/2011 | Roelle | A61B 1/009 901/1 |
| 2012/0216615 A1* | 8/2012 | Andersen | G01P 15/093 73/514.27 |
| 2015/0135832 A1* | 5/2015 | Blumenkranz | G02B 6/34 73/514.26 |
| 2015/0160725 A1 | 6/2015 | Lee et al. | |
| 2015/0310253 A1 | 10/2015 | Agrawal et al. | |
| 2015/0327940 A1* | 11/2015 | Inoue | A61B 34/30 606/130 |
| 2016/0157939 A1* | 6/2016 | Larkin | A61B 5/065 600/424 |
| 2016/0202285 A1* | 7/2016 | Wang | G01H 9/004 250/227.14 |
| 2016/0270655 A1 | 9/2016 | Caraffi et al. | |
| 2016/0349044 A1* | 12/2016 | Marell | G01B 21/045 |
| 2016/0370177 A1* | 12/2016 | Laine | G01B 11/16 |
| 2017/0031435 A1 | 2/2017 | Raffle et al. | |
| 2017/0086834 A1* | 3/2017 | Auld | A61B 17/07207 |
| 2017/0316264 A1 | 11/2017 | Gustafsson et al. | |
| 2019/0143506 A1 | 5/2019 | Rabindran et al. | |
| 2019/0183587 A1* | 6/2019 | Rafii-Tari | A61B 34/30 |
| 2019/0274768 A1* | 9/2019 | Fuerst | A61B 34/37 |
| 2019/0307517 A1* | 10/2019 | Arai | A61B 34/35 |
| 2020/0300614 A1* | 9/2020 | Van Putten | G01B 11/18 |
| 2021/0048355 A1* | 2/2021 | Hane | A61B 1/00097 |

OTHER PUBLICATIONS

International Search Report and Written Opinion for Application No. PCT/US2019/048628, mailed on Nov. 15, 2019, 14 pages.

Jang M., et al., "Towards Finger Motion Capture System Using FBG Sensors", 40th Annual International Conference of the IEEE Engineering in Medicine and Biology Society (EMBC), IEEE, Jul. 18, 2018, pp. 3734-3737.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Chien C-Y., et al., "FlexiBend: Enabling Interactivity of Multi-Part, Deformable Fabrications Using Single Shape-Sensing Strip," ACM UIST '15, Nov. 8-11, 2015, Retrieved from Internet: URL: http://www.cmlab.csie.ntu.edu.tw/~howieliang/FlexiBend/UIST15_FlexiBend.pdf,5 pages.

International Preliminary Report on Patentability for Application No. PCT/2019/043857, mailed on Feb. 11, 2021, 11 pages.

Shape Sensor and Shape Tape Technology, SPARE, Measurand Inc, 2000, retrieved from Internet: URL: http://www.spare.it/tn_meas.htm, 5 pages.

* cited by examiner

SYSTEMS AND METHODS FOR CONTROLLING A ROBOTIC MANIPULATOR OR ASSOCIATED TOOL

CROSS-REFERENCE TO RELATED APPLICATIONS

This application is the U.S. national phase of International Application No. PCT/US2019/043857, filed Jul. 29, 2019, which designated the U.S. and claims priority to and the benefit of U.S. Provisional Application No. 62/713,297 Aug. 1, 2018, both of which are incorporated by reference herein in their entirety.

FIELD

The present disclosure is directed to systems and methods for performing a robotic medical procedure and more particularly to systems and methods for controlling a medical tool.

BACKGROUND

Robotic manipulator assemblies can be operated to control motion of tools in a workspace. For example, such robotic manipulators can be used to perform non-medical and medical procedures. As a specific example, teleoperated surgical manipulators can be used to perform minimally invasive medical procedures.

It is desirable in medical techniques to reduce the amount of tissue that is damaged during medical procedures, thereby reducing patient recovery time, discomfort, and harmful side effects. For example, minimally invasive techniques may be performed through natural orifices in a patient anatomy or through one or more incisions. Through these natural orifices or incisions, clinicians may insert medical tools to reach a target tissue location. Minimally invasive medical tools include tools such as therapeutic tools, diagnostic tools, and surgical tools. Minimally invasive medical tools may also include imaging tools such as endoscopic tools that provide a user visualization within the patient anatomy.

Robotic manipulators may be teleoperated or otherwise computer-assisted. In some examples, a tool may be held by a robotic manipulator assembly for performing a procedure. For some examples, the tool and robotic manipulator are a single element. An operator may use one or more operator controllers (e.g., hand operator controllers) to control the robotic manipulator assembly, thereby controlling the tool. Thus, systems and methods are desired to provide better tracking of these operator controllers for better control of these tools, or of manipulator assemblies that support and operate these tools. These systems and methods may provide highly accurate real time position, orientation, and motion tracking of the operator controllers for controlling the tool in medical and non-medical contexts.

SUMMARY

The embodiments of the invention are summarized by the claims that follow below.

In one illustrative embodiment, a system includes a tool, an input device, a shape sensor system, and a processing unit. The processing unit is configured to determine a state estimate of the input device based on shape information from the shape sensor system, and control the tool based on the state estimate.

In another illustrative embodiment, a method includes receiving shape information from a shape sensor system. The shape sensor system is associated with a connection structure connecting an input device and a base. The method further includes determining a state estimate of the input device based on the shape information and controlling a tool based on the state estimate of the input device.

In another illustrative embodiment, a non-transitory machine-readable medium comprising a plurality of machine-readable instructions which, when executed by one or more processors, are adapted to cause the one or more processors to perform a method. The method includes receiving shape information from a shape sensor system. The shape sensor system is associated with a connection structure connecting an input device and a base. The method further includes determining a state estimate of the input device based on the shape information and controlling a tool based on the state estimate of the input device.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 1 provides a view of a surgical environment in which a teleoperational medical system operates in accordance with an embodiment of the present disclosure.

DETAILED DESCRIPTION

Figure 1:
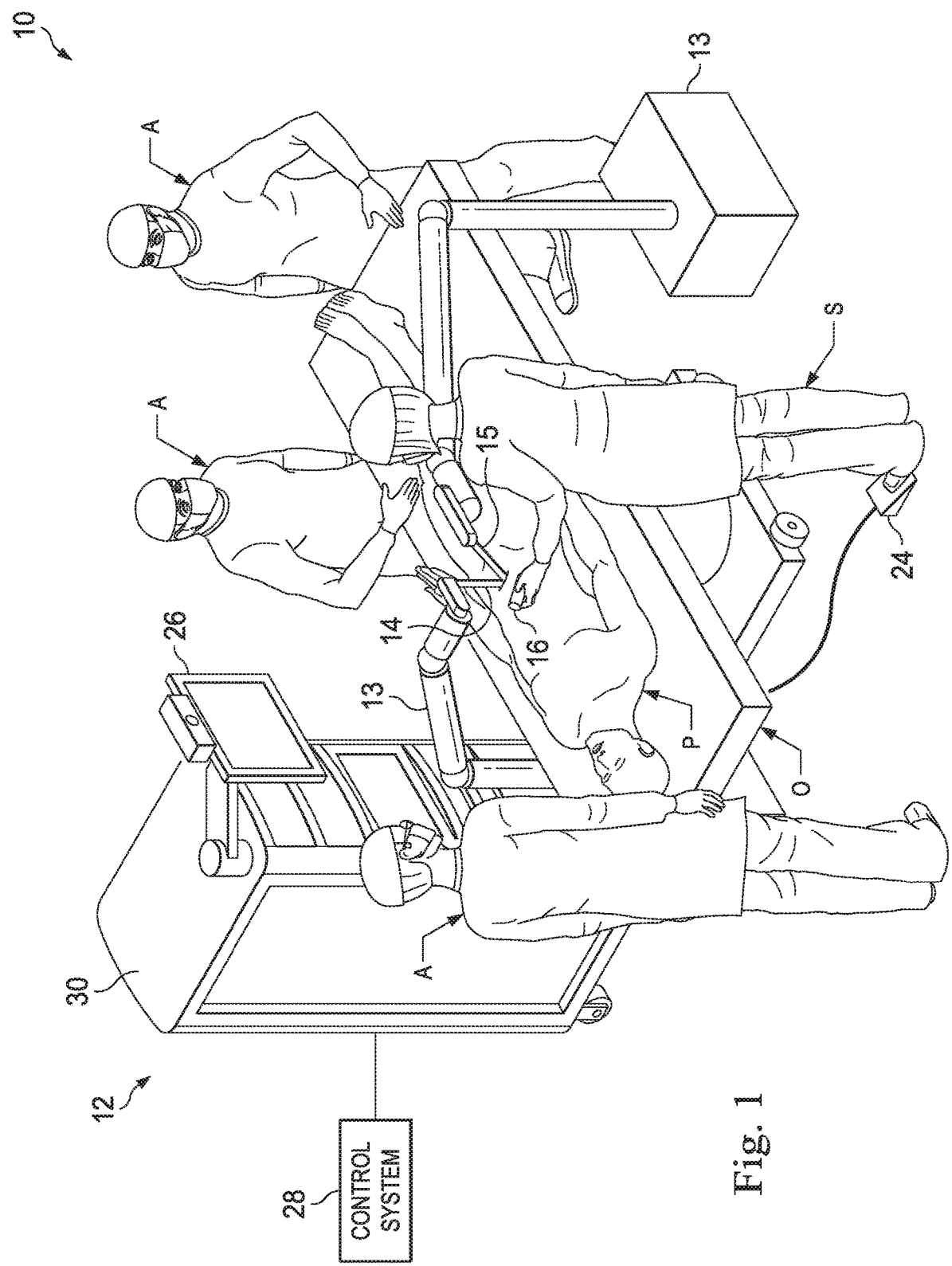

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances, well-known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances, the same reference numbers are used throughout the drawings to refer to the same or like parts.

The embodiments below will describe various instruments and portions of instruments in terms of their state in three-dimensional space. As used herein, the term "position" refers to the location a three-dimensional space (e.g., three degrees of translational freedom that can be described using changes in Cartesian X, Y, Z coordinates, such as along Cartesian X, Y, Z axes). For example, the position may be of a point, a reference frame, an object, or a portion of an object. As used herein, the term "orientation" refers to the rotational placement (three degrees of rotational freedom—e.g., which can be described using roll, pitch, and yaw). For example, the orientation may be of a reference frame, an object, or a portion of an object. As used herein, the term "pose" refers to the position and the orientation. For example, the pose of a reference frame, an object, or a portion of an object would include both position and orientation information of such reference frame, object, or portion of the object. In a three-dimensional space, a full pose can be described with six mathematically independent degrees of freedom. As used herein, the term "velocity" refers to the first time derivative of pose in general and "acceleration" refers to the second time derivative of pose in general, unless otherwise specified. The term "order" refers to the level of the differentiation with respect to time. For example, velocity is a first order property or signal and acceleration is a second order property or signal. "Higher-order" refers to second or higher order and "lower-order" refers to less than second order. As used herein, the term "shape" refers to a set of poses, positions, or orientations measured along an object.

As used herein, the term "estimate" of a signal refers to a direct measurement of the signal or numerically or analytically computation of the signal using different measurements, filtered measurements, and/or a combination thereof. The term "fused" or "fusion" of a plurality of signals refers to combining the plurality of signals, using methods including, for example, arithmetic average, weighted mean, linear or non-linear combination, and Kalman filter with or without the use of additional mathematical models.

Also, although some of the examples described herein refer to surgical procedures or tools, or medical procedures and medical tools, the techniques disclosed apply to non-medical procedures and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical, medical treatment or diagnosis procedures.

Referring to FIG. 1 of the drawings, an example medical environment with an exemplary system is shown. Specifically, FIG. 1 shows a surgical environment 10 that includes a teleoperational medical system 12 for use in, for example, medical procedures such as diagnostic, therapeutic, or surgical procedures. The surgical environment 10 can be described with a surgical coordinate space, and thus can be said to define the surgical coordinate space. The teleoperational medical system 12 generally includes a teleoperational assembly 13 (e.g., an instrument manipulator) mounted to or near an operating table O on which a patient P is positioned. The teleoperational assembly 13 may include one or more modular or integral manipulator arms. A tool 14 (e.g., a medical instrument, an endoscopic camera) or an endoscopic imaging system 15 may be operably coupled to a teleoperational manipulator (e.g. an arm) of the teleoperational assembly 13. An operator input system 16 allows an operator such as a surgeon or other type of clinician S to control the operation of the tool 14 and/or the endoscopic imaging system 15. One or more assistant surgeons, anesthesiologists, or support personnel A may also be present in the surgical environment.

For simplicity of explanation, much of this application refers to the person S as an operator, and the person A as an assistant. However, it should be understood that, where specialized surgical or assistant skills are not required, the person S may be a surgeon, some other clinician, some other medical personnel, some non-medical operator, or some other person. Similarly, the person A may be an assistant surgeon, some other clinician, some other medical personnel, some non-medical operator, or some other person. Also, where the procedure performed is not on a patient (e.g. for an industrial application, for training, for work on a cadaver or anatomy removed from and not to be returned to a patient, etc.), the persons S and A may have little or no medical training or knowledge.

A display system 26 may present images captured by the endoscopic imaging system 15, surgical navigation and guidance images, and/or alphanumeric or symbolic information to assist the personnel with the surgical procedure. The teleoperational medical system 12 also includes a control system 28 (processing unit) in communication with the operator input system 16, the teleoperational assembly 13 and the display system 26, as described below.

Figure 2:
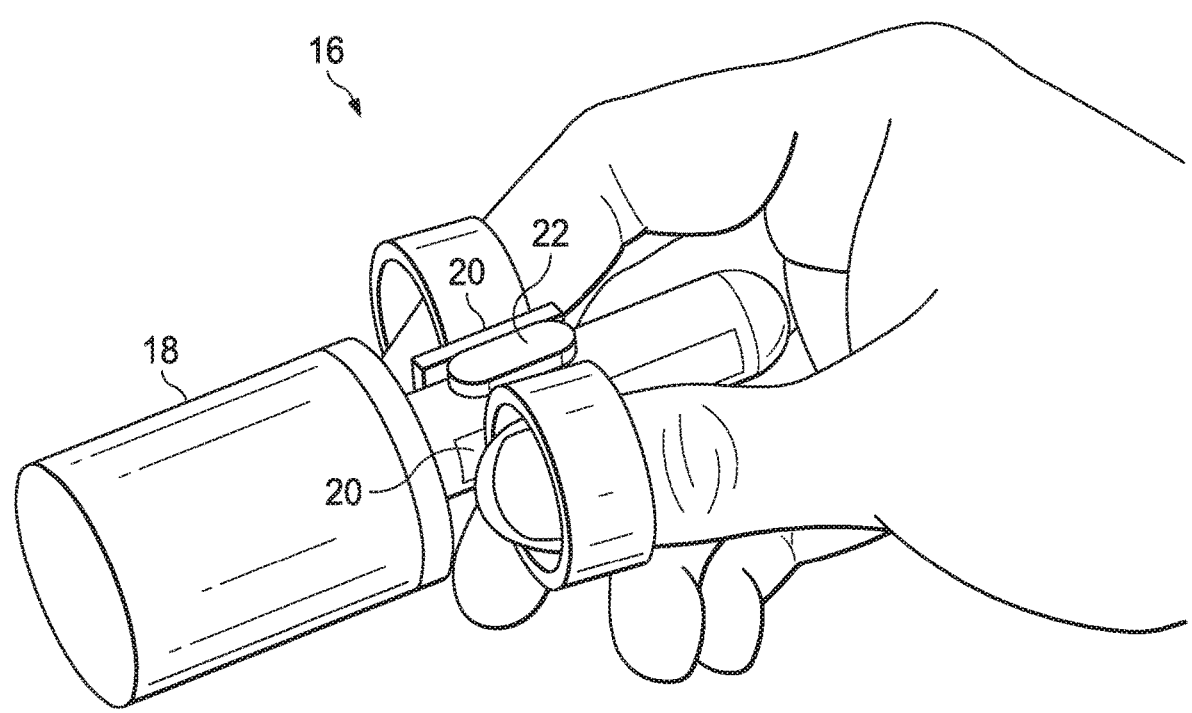
FIG. 2 illustrates an operator controller according to an embodiment of the present disclosure.

In this embodiment, the operator input system 16 includes one or a set of operator hand controllers 18 (FIG. 2) for controlling one or multiple tools 14 and/or 15. The input system also, optionally, includes a pedal control device 24. The operator hand controllers 18 and the pedal control device 24 may be located at the side of the patient P. In various alternatives the operator hand controllers 18 may be tethered by power and/or signal transmission cabling or may be untethered/wireless. In other alternative embodiments, the operator hand controllers 18 may be located at an operator's console such as an operator's console, which may be located in the same room as operating table O. As shown in FIG. 2, the operator hand controllers 18 may include one or more of any number of a variety of input devices such as grip levers 20 and trigger switches 22. The input devices may be used to, for example, close grasping jaw end effectors, apply an electrical potential to an electrode, deliver a medicinal treatment, or the like. In various alternatives, the operator input system 16 may additionally or alternatively include joystick devices, trackballs, data gloves, trigger-guns, hand-operated controllers, voice recognition devices, touch screens, body motion or presence sensors, and the like. In some embodiments, the operator hand controllers 18 will be provided with the same degrees of freedom as the medical instruments of the teleoperational assembly to provide the operator S with telepresence, the perception that the control device(s) are integral with the instruments so that the operator S has a strong sense of directly controlling instruments as if present at the surgical site. In other embodiments, the operator hand controllers 18 may have more or fewer degrees of freedom than the associated medical instruments and still provide the surgeon or another operator with telepresence. Although hand controller 18 has been described here for a medical system, hand controller 18, or other input devices similar to hand controller 18, can be used in non-medical systems as well.

The teleoperational assembly 13 supports and manipulates the tool 14 while the operator S conducts the procedure from the patient side or another location within the surgical environment. An image of the surgical site within the patient can be obtained by the endoscopic imaging system 15, such as a stereo endoscopic imaging system, which can be manipulated by the teleoperational assembly 13 to orient the endoscopic imaging system 15. The number of tools 14 used at one time will generally depend on the diagnostic or surgical procedure and the space constraints within the operating room among other factors. Each arm of the teleoperational assembly 13 may include a kinematic structure of one or more servo or non-servo controlled joints and/or links. The teleoperational assembly 13 includes a plurality of motors that drive inputs on the tool 14. These motors move in response to commands from the control system 28. The motors include drive systems, which when coupled to the tool 14 may advance the tool 14 into a naturally or surgically created anatomical orifice. Other motorized drive systems may move the distal end of the tool 14 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the tool 14 for grasping tissue in the jaws of a biopsy device or the like. Tools 14 may include end effectors having a single working member such as a scalpel, a blunt blade, a needle, an imaging sensor, an optical fiber, an electrode, etc. Other end effectors may include multiple working members, and examples include forceps, graspers, scissors, clip appliers, staplers, bipolar electro-cautery instruments, etc.

The control system 28 includes at least one memory and at least one processor, and typically a plurality of processors, for effecting control between the tools 14, the endoscopic imaging system 15, the operator input system 16, the display system 26, and other auxiliary systems which may include, for example, hand-held medical instrument systems, additional imaging systems, audio systems, fluid delivery systems, display systems, illumination systems, steering control systems, irrigation systems, and/or suction systems. The control system 28 also includes programmed instructions (e.g., a computer-readable medium storing the instructions) to implement some or all of the methods described in accordance with aspects disclosed herein. While the control system 28 is shown as a single block in the simplified schematic of FIG. 1, the control system 28 may include two or more data processing circuits with one portion of the processing optionally being performed on or adjacent the teleoperational assembly 13, another portion of the processing being performed at the operator input system 16, and the like. In various embodiments, the control system 28 may be housed in an electronics cart 30 to which the display system 26 or other peripheral equipment is mounted. The control system 28 may employ any of a wide variety of centralized or distributed data processing architectures. Similarly, the programmed instructions may be implemented as a number of separate programs or subroutines, or they may be integrated into a number of other aspects of the teleoperational medical systems described herein. In one embodiment, the control system 28 supports wireless communication protocols such as Bluetooth, IrDA, HomeRF, IEEE 802.11, DECT, and Wireless Telemetry.

In some embodiments, the control system 28 may include one or more controllers that receive force and/or torque feedback from the tool 14. Responsive to the feedback, the controllers transmit signals to the operator input system 16. The controller(s) may also transmit signals instructing teleoperational assembly 13 to move the medical instrument system(s) 14 and/ or endoscopic imaging system 15 which extend into an internal surgical site within the patient body via openings in the body. Any suitable conventional or specialized controller may be used. A controller may be separate from, or integrated with, the teleoperational assembly 13. In some embodiments, the controller and teleoperational assembly 13 are provided as part of a teleoperational arm positioned adjacent to the patient's body.

The control system 28 can be coupled with the endoscopic imaging system 15 and can include a processor to process captured images for subsequent display, such as to an operator S the display system 26, on the operator's console, or on another suitable display located locally and/or remotely. For example, where a stereo endoscopic imaging system is used, the control system 28 can process the captured images to present the surgeon or some other personnel with coordinated stereo images of the surgical site. Such coordination can include alignment between the opposing images and can include adjusting the stereo working distance of the stereoscopic endoscope.

In alternative embodiments, the teleoperational medical system 12 may include more than one teleoperational assembly 13 and/or more than one operator input system 16. The exact number of teleoperational assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Referring to FIGS. 3 through 10, various sensor systems (e.g., a shape sensor system, a local sensor system) may be used to determine state (e.g., pose, motion) estimates of the input device, which may be used by a control system to control one or multiple tools. For example, a shape sensor system may be used for providing estimates of states (e.g., pose, motion) of an input device and/or states (e.g., pose, motion, shape) of one or more segments along a connection structure (e.g., a flexible body, a kinematic chain) connecting the input device and a base. While in the examples described herein, the tools are medical tools, noted above, these techniques also apply to a variety of non-medical uses using non-medical tools such as an industrial tool, and entertainment tool, a teaching tool, or some other a non-medical tool.

Figure 7:
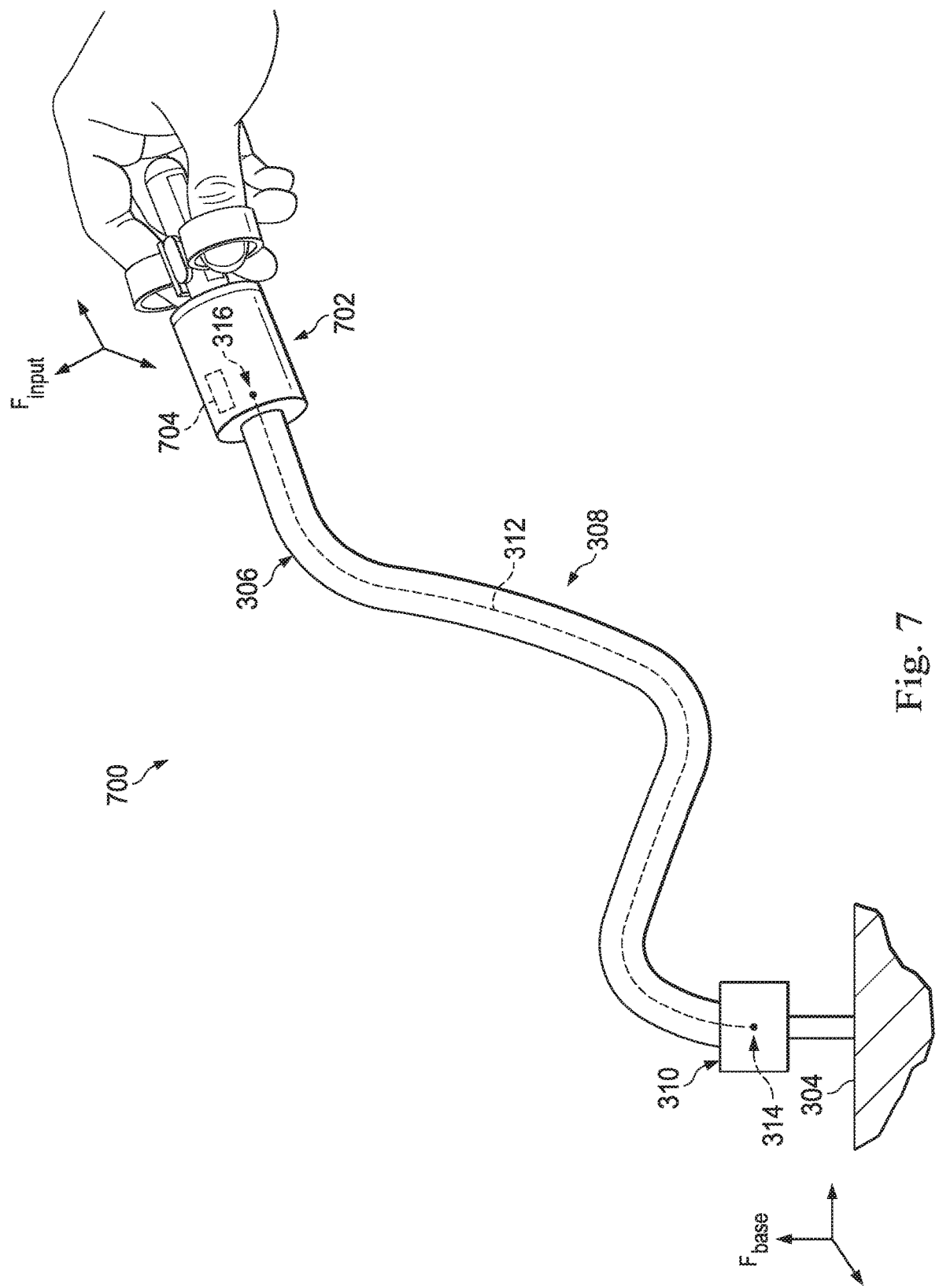
FIG. 7 illustrates an operator input system according to an embodiment of the present disclosure.
Figure 8:
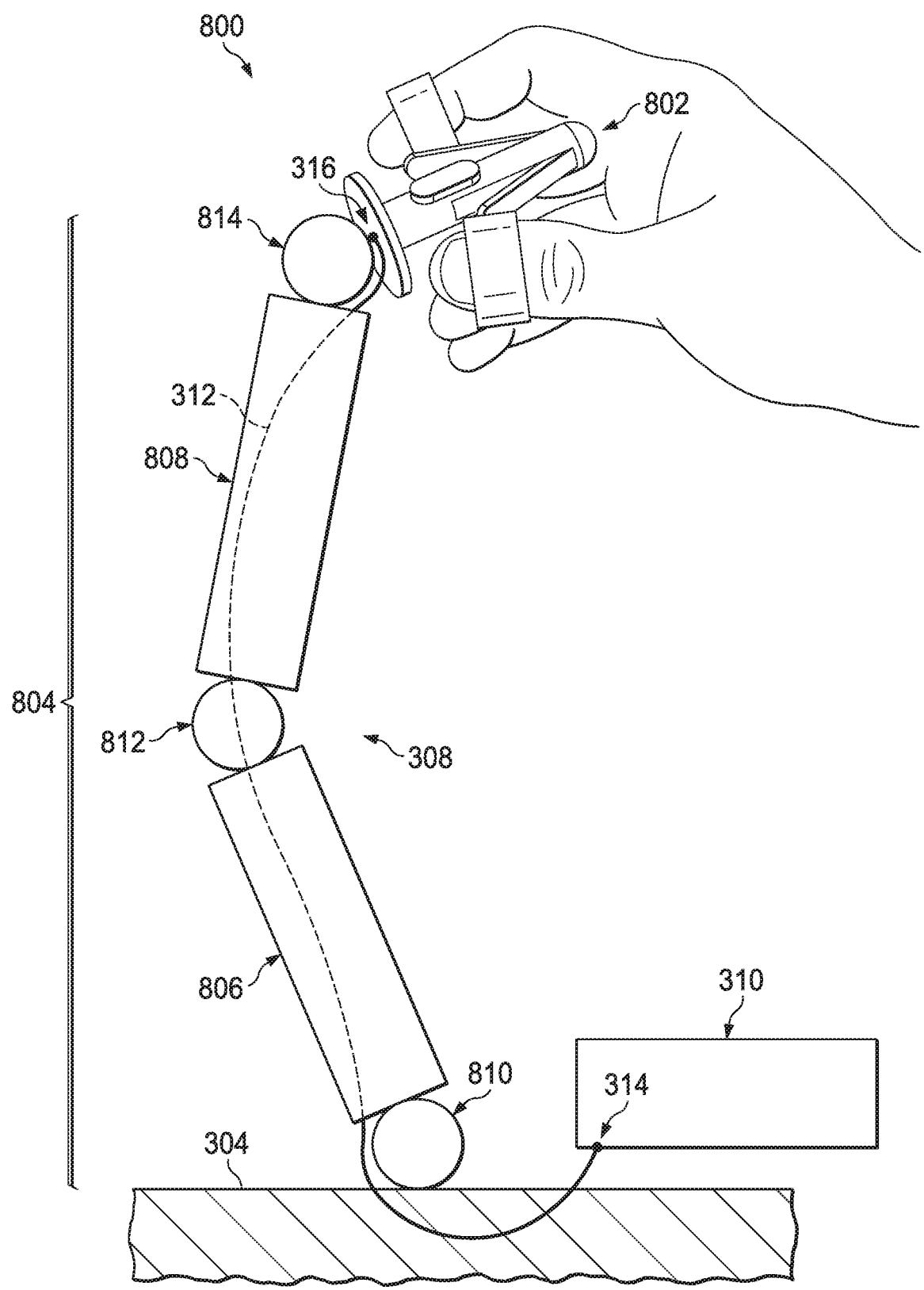
FIG. 8 illustrates an operator input system according to an embodiment of the present disclosure.
Figure 9:
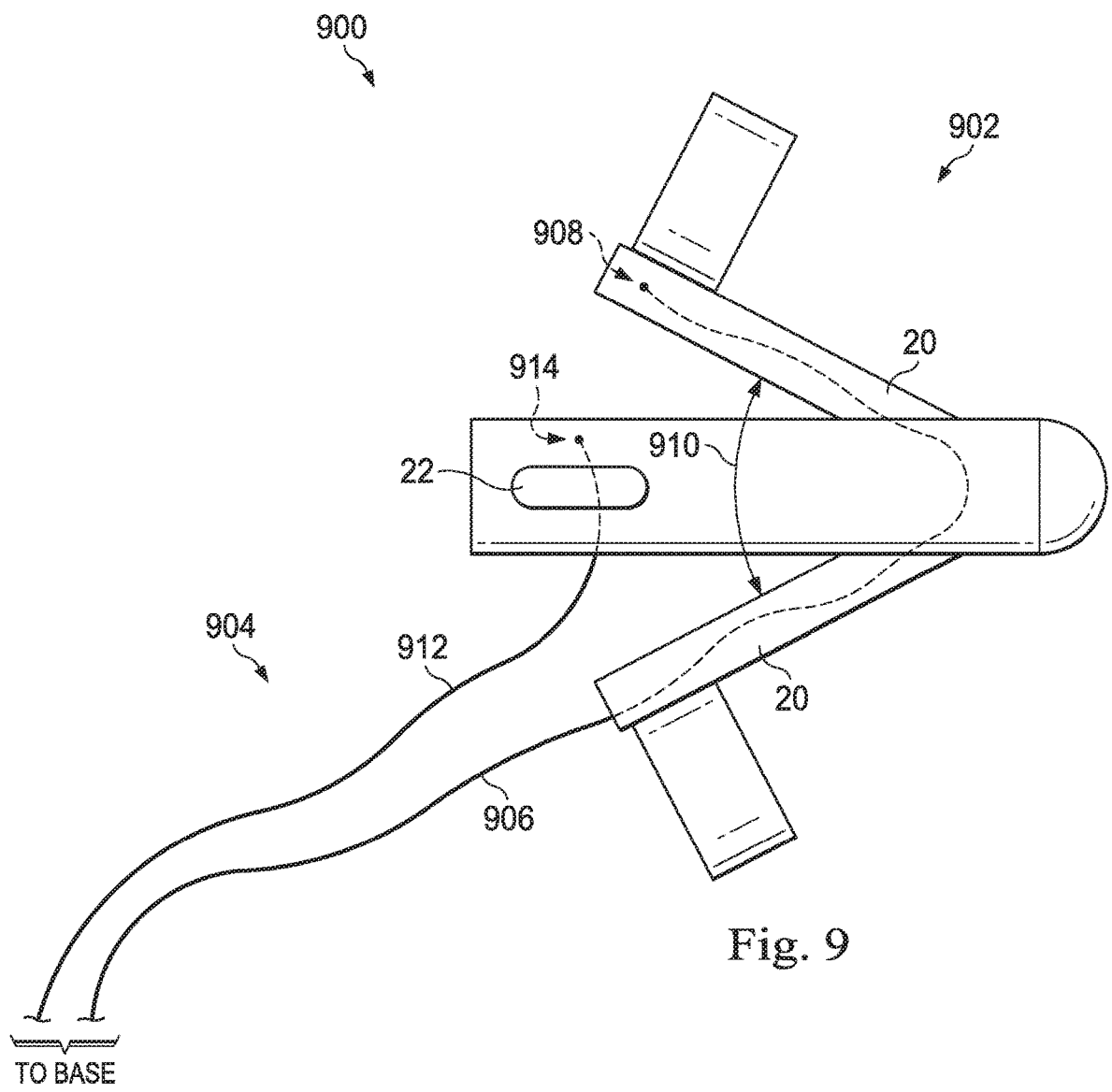
FIG. 9 illustrates an operator input system according to an embodiment of the present disclosure.
Figure 10:
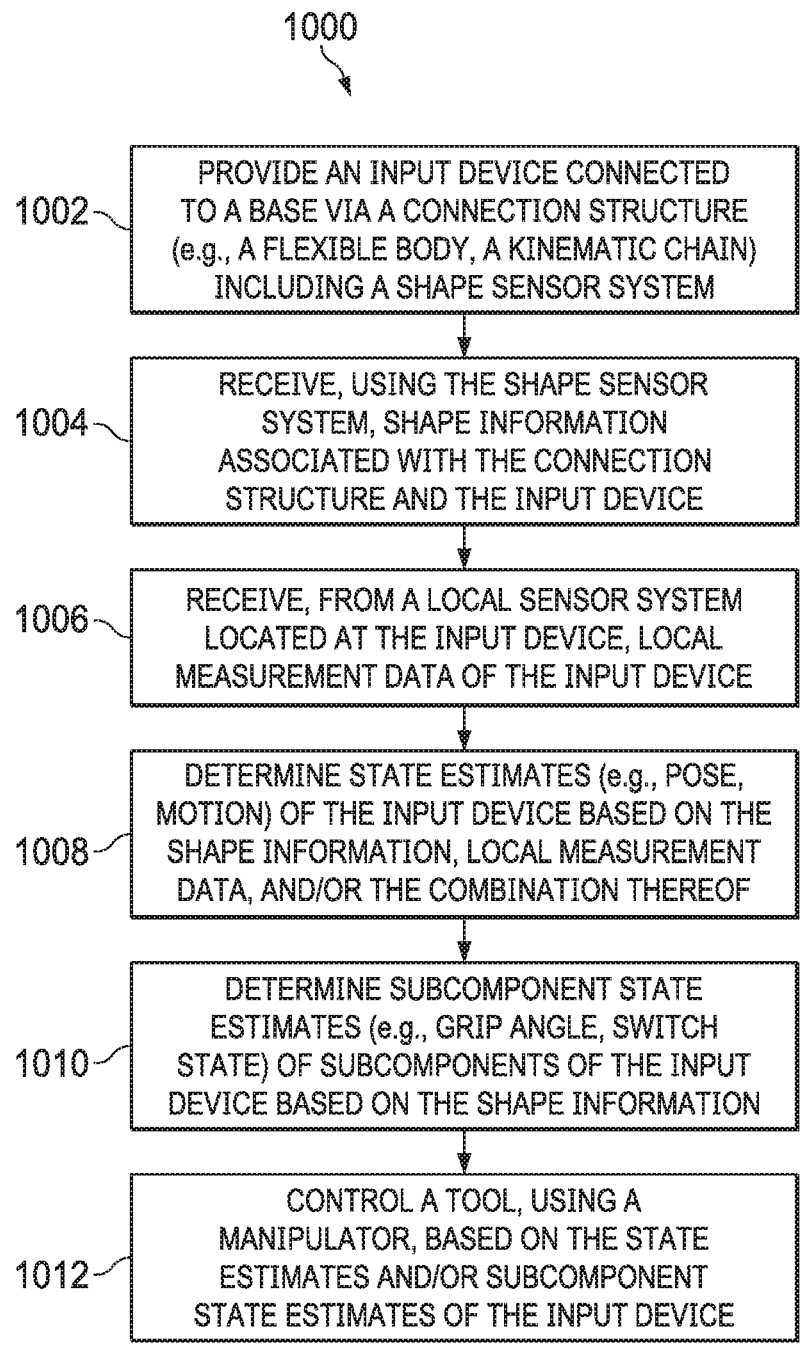
FIG. 10 is a flowchart providing a method for controlling a tool using an operator input system according to an embodiment of the present disclosure.

In the examples of FIGS. 3, 4, 5, and 6, a shape sensor system is used to provide shape information associated with the input device for determining the input from an input device, where the input device is connected to a base via a connection structure (e.g., an umbilical) containing the shape sensor system. In the example of FIG. 7, a local sensor system located at the input device may be used to provide local measurement data of the input device for determining the input from an input device. In the example of FIG. 8, an input device is "mechanically grounded" by being connected to a base with a connection structure including a kinematic chain, where a shape sensor system is used to determine the configuration of the kinematic chain for determining the input from the input device. In the example of FIG. 9, a shape sensor system is used to provide shape information associated with an input device for determining a grip angle of the input device. FIG. 10 includes a flow chart illustrating a method for using the various sensor systems to determine the input from the input device for controlling the tool.

Figure 3:
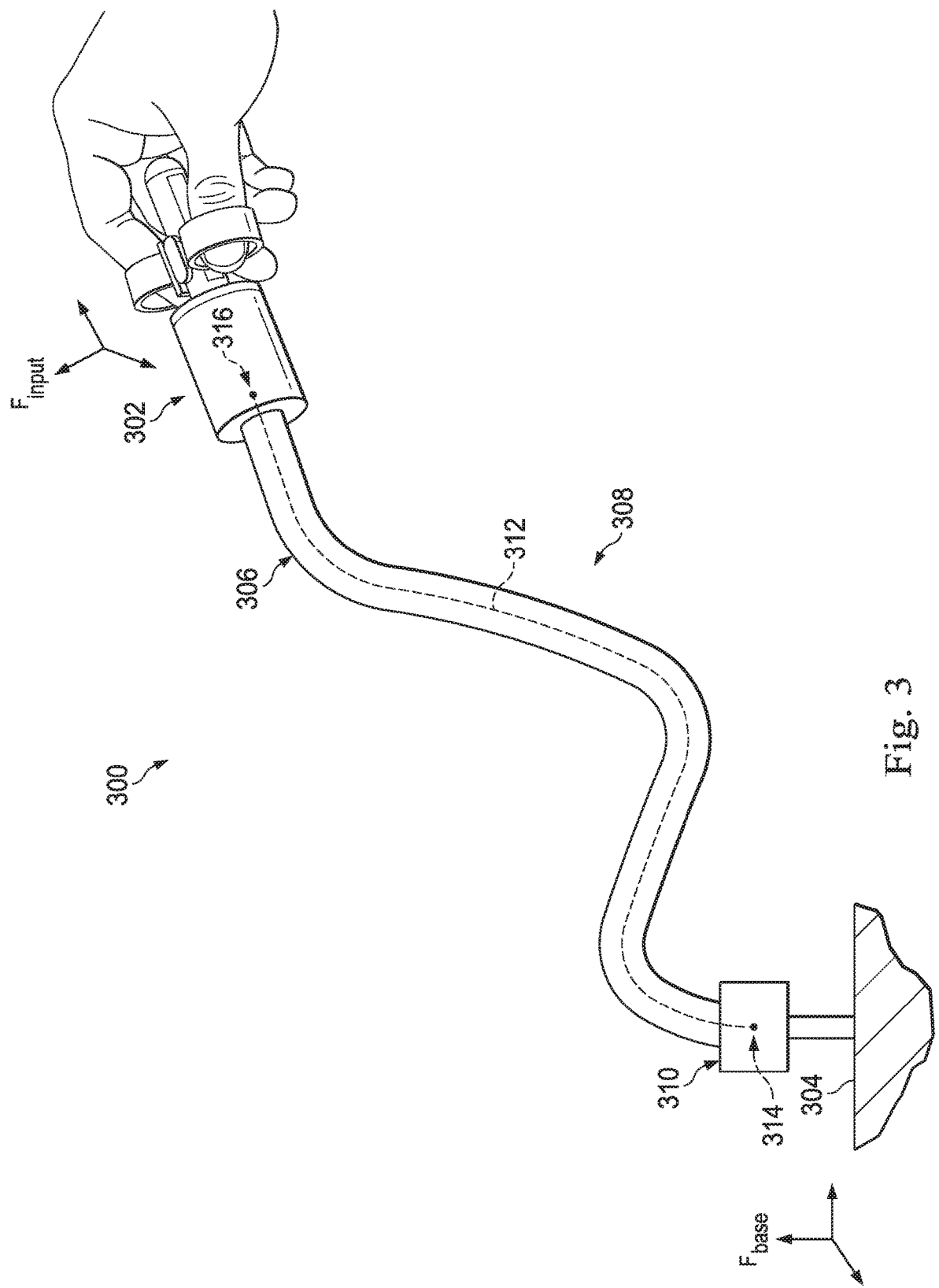
FIG. 3 illustrates an operator input system according to an embodiment of the present disclosure.

Referring to the example of FIG. 3, an operator input system 300 (e.g., an operator input system 16 of FIGS. 1 and 2) includes an input device 302 (e.g., an operator hand controller 18 of FIG. 2). The input device 302 is connected to a base 304 via a connection structure 306. In the example of FIG. 3, the connection structure 306 is a flexible body (e.g., an umbilical), and is also referred to as a flexible body 306. The flexible body 306 includes a shape sensor system 308. The shape sensor system 308 includes a shape sensing fiber 312 having a proximal end 314 and a distal end 316. The proximal end 314 of the shape sensing fiber 312 is physically (e.g., mechanically) fixed relative to the base 304 (e.g., by physically fixed directly at the base 304 or physically fixed directly at an interrogator system 310 that is physically fixed to the base 304). The distal end 316 of the shape sensing fiber 312 is physically fixed relative to the input device 302.

In some embodiments, an interrogator system 310 is coupled to the shape sensor system 308. In the example of FIG. 3, the interrogator system 310 is physically fixed to the base 304. A portion (e.g., proximal end 314) of the shape sensing fiber (e.g., shape sensing fiber 312) may be physically fixed relative to the base 304 by directly fixed to the interrogator system 310. In some embodiments, the interrogator system 310 is used to sense strain information associated with the shape sensor system 308. A control system (e.g., a control system 28 of FIG. 1) may receive the strain information from the interrogator system 310 for determining the shape information. The control system may integrate the shape information along the length of the shape sensing fiber 312, for example, from its proximal end 314 to the distal end 316. The control system may use the shape information including, for example, changes in shape, to generate state estimates (e.g., pose, motion (e.g., velocity, acceleration, and angular velocity)) of the input device 302 in an input device reference frame $F_{input}$ that is rigidly fixed to the input device relative to a base reference frame $F_{base}$ associated with the base 304.

In various embodiments, the state estimates of the input device 302 are updated periodically by the control system based on the real time shape information. The control system may use the state estimates of the input device 302 to control the tool. In some embodiments, the control system may perform a calibration process to compensate for uncertainties in the relationship between the shape sensing fiber proximal end 314, distal end 316, the input device reference frame $F_{input}$, and base reference frame $F_{base}$.

In some embodiments, in addition to a light for shape sensing, the shape sensing fiber of the shape sensor system 308 may be used to deliver a visible light to provide state indications of the input device to an operator. This visible light may be different (e.g., having a different frequency/wavelength) from the light for shape sensing. The visible light from the shape sensing fiber may illuminate a part of the input device to provide the state indications. The delivered light may be used to indicate whether the input device is actively used to control a manipulator, whether the input device is in a clutched state, whether the input device is correctly aligned, whether particular criteria have been satisfied to transition into different operation modes (e.g., follow mode), whether there is a need to locate an input device interface in a darkened operating room, etc. A wavelength of such light may be determined so that the light for state indication may not interfere with shape sensing interrogation and/or may be suitable for transmitting to the distal end of the shape sensing fiber for visual indication. In some embodiments where the shape sensor system 308 includes a plurality of shape sensing fibers, each of these shape sensing fibers may be used to provide a separate state indication. In some embodiments, a plurality of bands of light may be used in a single shape sensing fiber to provide state indications (e.g., switch states of the input device).

Figure 4:
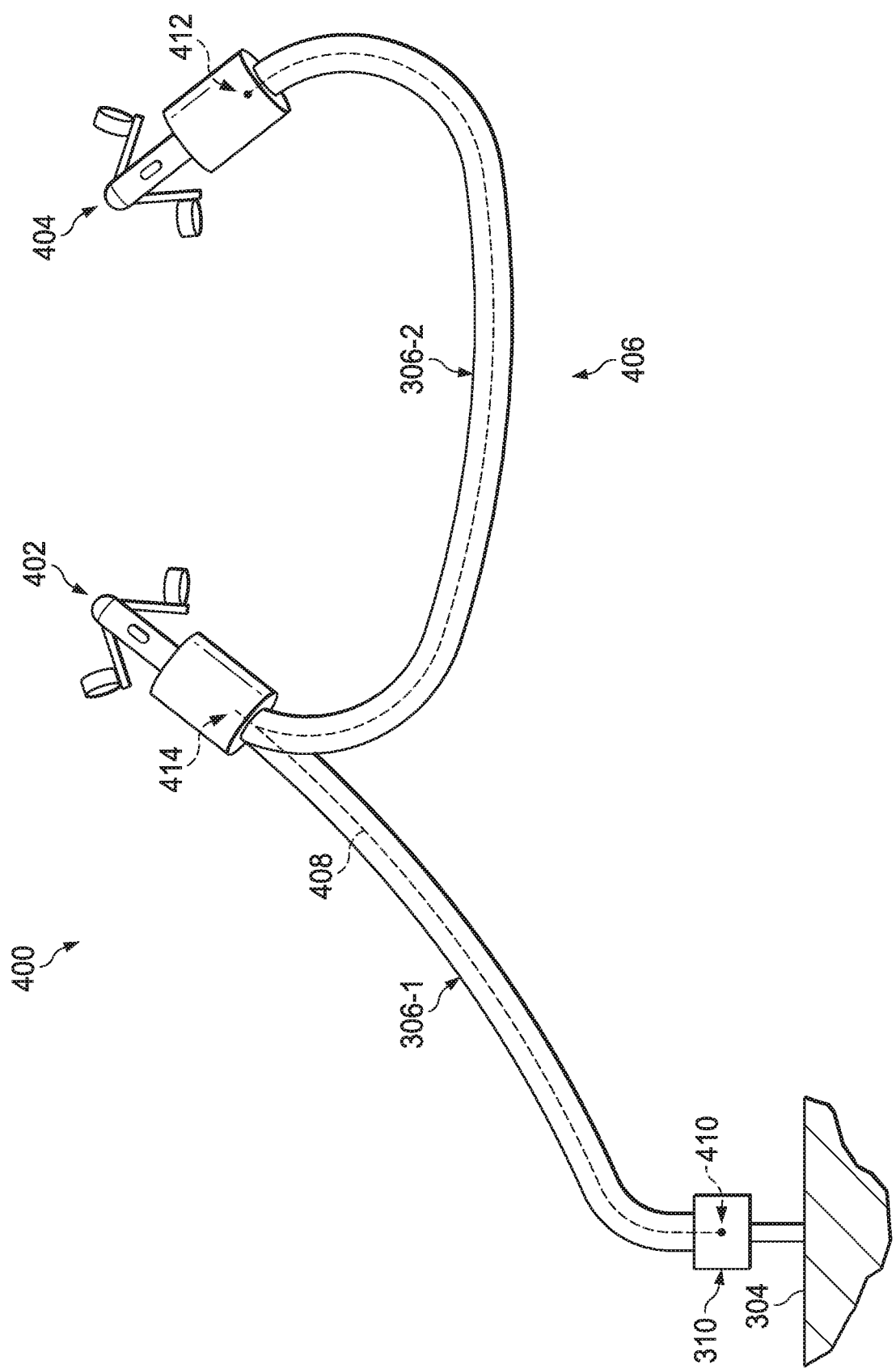
FIG. 4 illustrates an operator input system according to an embodiment of the present disclosure.

Referring to FIG. 4, in some embodiments, an operator input system 400 (e.g., an operator input system 16 of FIGS. 1 and 2) may include a hand controller 402 (e.g., a hand controller 18 of FIG. 2) configured to be moved by a first hand of an operator, and a hand controller 404 configured to be moved by another hand of the operator.

As illustrated in the example of FIG. 4, in some embodiments, a shape sensor system 406 may include a single shape sensing fiber 408 that is routed through both hand controllers 402 and 404. In the example of FIG. 4, the hand controller 402 is connected to the base 304 via a segment 306-1 of a flexible body 306, and is connected to the hand controller 404 via a segment 306-2 of the flexible body 306. The flexible body 306 includes a shape sensor system 406, which includes a single shape sensing fiber 408 that is routed through both the hand controllers 402 and 404. Specifically, the shape sensing fiber 408 has a proximal end 410 physically fixed relative to the base 304, has a distal end 412 physically fixed relative to the hand controller 404, and has a portion 414 (e.g., located between the proximal end 410 and distal end 412) that is physically fixed relative to the hand controller 402.

In alternative embodiments, a shape sensor system may include separate shape sensing fibers for hand controllers 402 and 404 respectively. For example, the shape sensor system may include a first shape sensing fiber connecting the base 304 and the hand controller 402, where a proximal end of the first shape sensing fiber is physically fixed relative to the base 304, and a distal end of the first shape sensing fiber is physically fixed relative to the hand controller 402. For further example, the shape sensor system may include a second shape sensing fiber connecting the base 304 and the hand controller 402, where a proximal end of the first shape sensing fiber is physically fixed relative to the base 304, and a distal end of the first shape sensing fiber is physically fixed relative to the hand controller 404.

Figure 5:
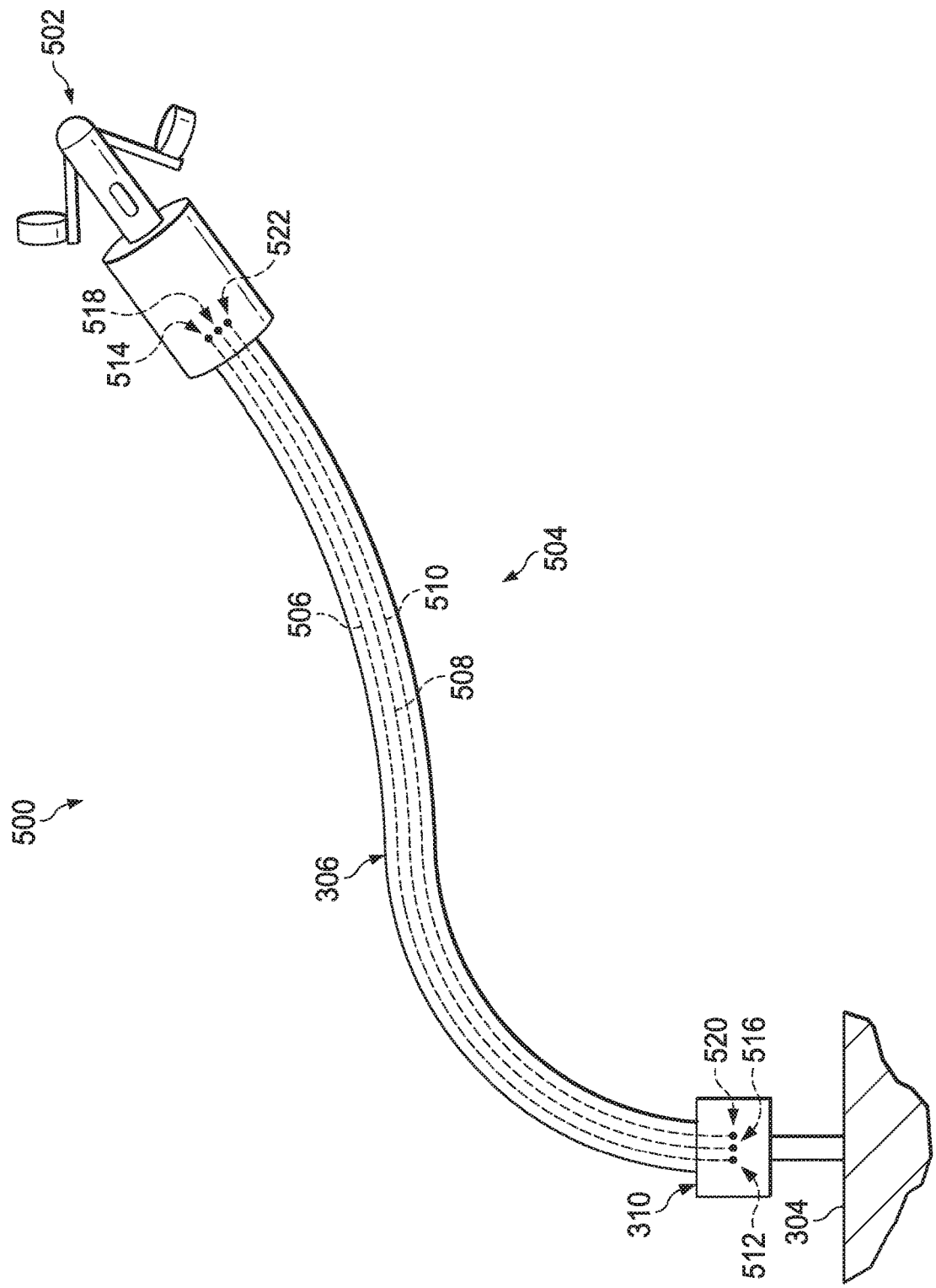
FIG. 5 illustrates an operator input system according to an embodiment of the present disclosure.
Figure 6:
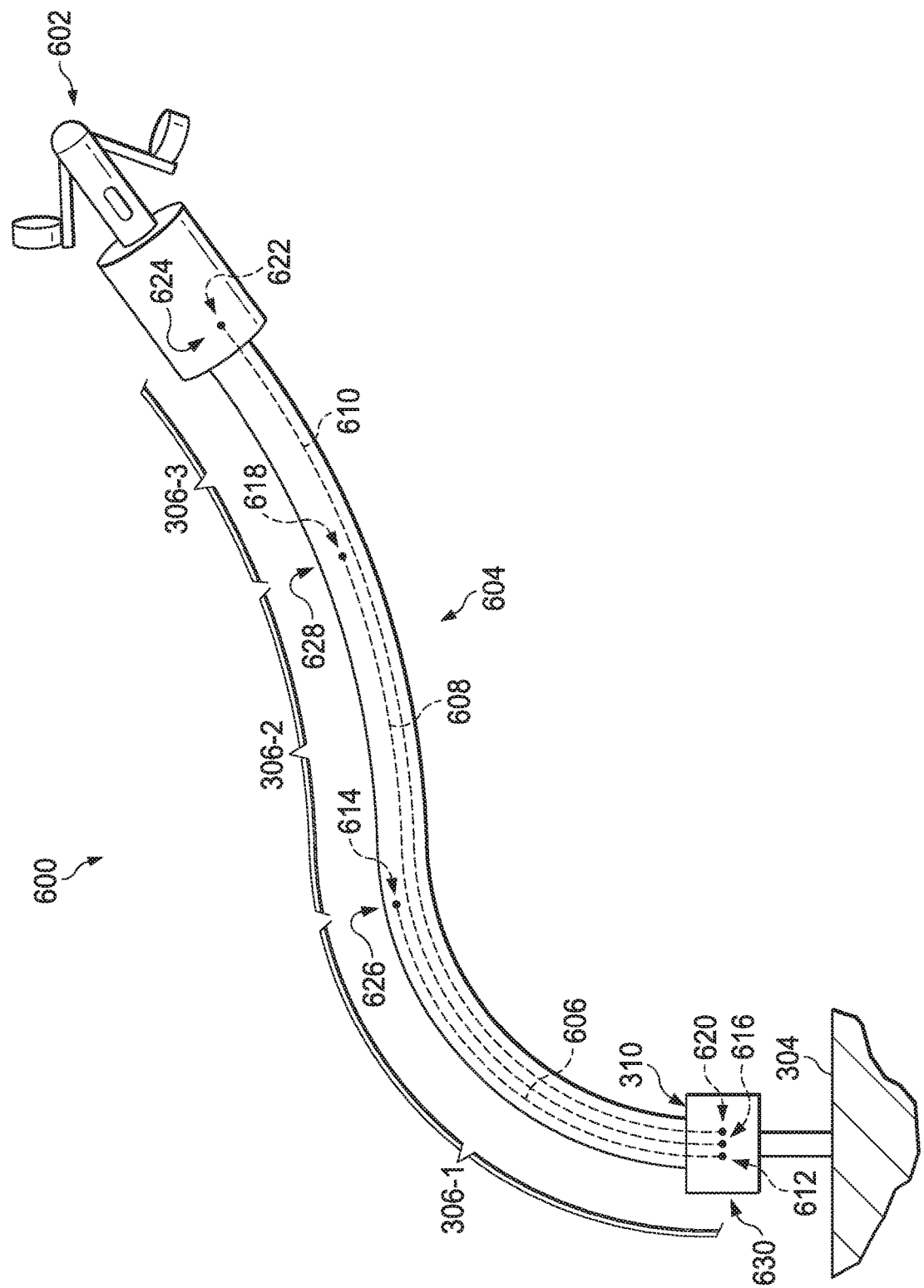
FIG. 6 illustrates an operator input system according to an embodiment of the present disclosure.

Referring to FIGS. 5 and 6, in some embodiments, a shape sensor system including multiple shape sensing fibers may be used to provide shape information for generating state estimates of the input device. A control system may generate state estimates of the input device by combining shape information from different shape sensing fibers of the shape sensor system in various ways. In some embodiments, multiple shape sensing fibers may be used for redundancy or multiple mode sensing. In some embodiments, multiple shape sensing fibers may be used to improve accuracy (e.g., where the flexible body to be measured by the shape sensor system has a long length) and reduce measurement noise, e.g., by combining state estimates (e.g., by averaging pose and/or motion estimates) from the multiple shape sensing fibers. In some embodiments, multiple shape sensing fibers may be stacked such that a shape sensing fiber having a smaller diameter is located distally while another sensing fiber having a larger diameter is located proximately to enable a smaller radius of curvature of the flexible body closer to the input device.

In the example of FIG. 5, an operator input system 500 (e.g., an operator input system 16 of FIGS. 1 and 2) includes an input device 502 (e.g., an operator hand controller 18 of FIG. 2). The input device 502 is connected to a base 304 via a flexible body 306. The flexible body 306 includes a shape sensor system 504. The shape sensor system 504 includes shape sensing fibers 506, 508, and 510. As illustrated in FIG. 5, each of the shape sensing fibers 506, 508, and 510 is routed from the base to the input device 502. Specifically, the shape sensing fiber 506 has a portion 512 physically fixed relative to the base 304, and has a portion 514 physically fixed relative to the input device 502. The shape sensing fiber 506 has a portion 512 physically fixed relative to the base 304, and has a portion 514 physically fixed relative to the input device 502. The shape sensing fiber 508 has a portion 516 physically fixed relative to the base 304, and has a portion 518 physically fixed relative to the input device 502. The shape sensing fiber 510 has a portion 520 physically fixed relative to the base 304, and has a portion 522 physically fixed relative to the input device 502. While three shape sensing fibers are illustrated in the example of FIG. 5, any suitable number of fibers may be used.

In some embodiments, the control system generates state estimates of the input device by averaging the shape information from the different shape sensing fibers (e.g., shape sensing fibers 506, 508, and 510) of the shape sensor system, which may improve signal to noise performance, robustness, and/or redundancy. In alternative embodiments, the control system determines the combined shape information associated with the input device by processing the shape information from different shape sensing fibers differently. For example, filters (e.g., Kalman filters) tuned to low, medium, and high frequencies may be applied to shape information from the shape sensing fibers 506, 508, and 510 respectively. A first filter tuned to low frequency may be applied to first shape information from the shape sensing fiber 506, where the filtered first shape information is used for generating low frequency (e.g., around 1 Hz) motion estimates of the input device. A second filter tuned to medium frequency (e.g., around 5 Hz) may be applied to second shape information from the shape sensing fiber 508, where the filtered second shape information is used for generating medium frequency motion estimates of the input device. A third filter tuned to high frequency (e.g., around 20 Hz) may be applied to third shape information from the shape sensing fiber 510, where the filtered third shape information is used for generating high frequency motion estimates of the input device.

Referring to FIG. 6, in some embodiments, a shape sensor system may include multiple shape sensing fibers configured to provide shape information for different segments of the flexible body connecting the input device and the base. In the example of FIG. 6, an operator input system 600 (e.g., an operator input system 16 of FIGS. 1 and 2) includes an input device 602 (e.g., an operator hand controller 18 of FIG. 2). The input device 602 is connected to a base 304 via a flexible body 306. The entire length of flexible body 306 (e.g., between distal end 624 and proximal end 630) may be effectively divided into segments (e.g., segments 306-1, 306-2, and 306-3). In the example of FIG. 6, the segment 306-1 starts at proximal end 630, and ends at a location 626 of the flexible body 306. The segment 306-2 starts at the location 626 and ends at a location 628 of the flexible body 306. The segment 306-3 starts at the location 628 of the flexible body 306 and ends at the distal end 624.

In the example of FIG. 6, the flexible body 306 contains a shape sensor system 604 including shape sensing fibers 606, 608, and 622 with different lengths and configured to provide shape information for determining the shapes of the segments 306-1, 306-2, and 306-3. The shape sensing fiber 606 includes a portion 612 (e.g., a proximal end) physically fixed relative to the base 304, and a portion 614 (e.g., a distal end) physically fixed relative to the location 626 of the flexible body 306, which is the end of the segment 306-1. The shape sensing fiber 608 includes a portion 616 (e.g., a proximal end) physically fixed relative to the base 304, and a portion 618 (e.g., a distal end) physically fixed relative to a location 628 of the flexible body 306, which is the end of the segment 306-2. The shape sensing fiber 610 includes a portion 620 (e.g., a proximal end) physically fixed relative to the base 304, and a portion 622 (e.g., a distal end) physically fixed relative to the input device 602.

In the example of FIG. 6, a control system may determine a segment shape of the segment 306-1 based on shape information from the shape sensing fiber 606, determine a segment shape of the segment 306-2 based on shape information from the shape sensing fiber 608, and determine a segment shape of the segment 306-3 based on shape information from the shape sensing fiber 610. The control system may determine the shape of the flexible body 306 using the segment shapes of the segments 306-1, 306-2, and 306-3, and determine a pose of the input device 602 using the shape of the flexible body 306.

As shown in the example of FIG. 6, the stacking of the multiple shape sensing fibers may increase accuracy of the measurement. In some embodiments, a first shape sensing fiber having a shorter measurement length is more accurate than a second shape sensing fiber (e.g., having the same or similar properties of the first shape sensing fiber) having a longer length. In those embodiments, stacking multiple fibers, each measuring a portion of the shape sensing region along the length of the fiber(s) may improve measurement accuracy compared to using a single long fiber over the entire shape sensing region. For example, fiber 608 may actively measure shape only along the segment 306-2, while segment 306-1 of fiber 608 is an unsensed portion. Similarly, fiber 610 may measure shape only along segment 306-3 but not segments 306-2 or 306-1. In some examples, two or more segments may overlap.

In some embodiments, the stacking of the multiple shape sensing fibers may be used where the length of sensor portion of a fiber is limited and too short to span the total length of 306. In those embodiments, the shape along the entire length of 306 is measured in segments by 606, 608, and 610, with shape sensing regions along 306-1, 306-2, and 306-3 respectively.

Referring to FIG. 7, in some embodiments, a control system may determine state estimates of an input device based on both shape information from a shape sensor system connected to the input device and local measurement data from a local sensor system located at the input device. By combining measurement data from the shape sensor system and the local sensor system, the control system may provide faster and more accurate state estimates of the input device, thereby providing improved control of the tool.

In the example of FIG. 7, an operator input system 700 (e.g., an operator input system 16 of FIGS. 1 and 2) includes an input device 702 (e.g., an operator hand controller 18 of FIG. 2). The input device 702 is connected to a base 304 via a flexible body 306. The flexible body 306 includes a shape sensor system 308. The shape sensor system 308 includes a shape sensing fiber 312 having a proximal end 314 and a distal end 316. The proximal end 314 of the shape sensing fiber 312 is physically (e.g., mechanically) fixed relative to the base 304, and the distal end 316 of the shape sensing fiber 312 is physically fixed relative to the input device 302.

In the example of FIG. 7, the operator input system 700 may include a local sensor system 704 located at the input device 702. The local sensor system 704 may include one or more sensors including, for example, an inertial measurement unit (IMU), an electromagnetic sensor, a hybrid sensor system incorporating two or more sensing technologies, other suitable sensor systems, and a combination thereof. In some examples, the IMU may include an accelerometer configured to measure the linear acceleration of the input device 702, and a gyroscope configured to measure the angular velocity of the input device 702. The local sensor system 704 may provide local measurement data of the input device (e.g., pose data, acceleration data, and angular velocity data of input device 702) to the control system. The local sensor system 704 may include one or more IMUs, accelerometers, gyroscopes, magnetometers, and/or a combination thereof.

In some embodiments, the distal end 316 of the shape sensor system 308 and the location of the local sensor system 704 are physically fixed with respect to one another. In some embodiments, the control system may use a calibration algorithm to calibrate the fixed transformation between a shape sensor termination frame fixed to the distal end 316 of the shape sensor system 308 and a local sensor frame of reference.

In some embodiments, a control system generates state estimates of the input device 702 using both the shape information from the shape sensor system 308 and the local measurement data from the local sensor system 704. In some examples, the control system may generate state estimates of the input device 702 by generating low frequency state estimates of the input device based on the shape information from the shape sensor system 308, and generating high frequency state estimates of the input device 702 based on the local measurement data from the local sensor system 704. In those examples, the local sensor system 704 (e.g., an IMU) may provide accurate motion measurement data (e.g., acceleration, angular velocity) of the input device 702 with low latency, but may be subject to drift when measuring pose (e.g., position, orientation) of the input device 702. On the other hand, the shape sensor system 308 may be configured to provide pose measurement data associated with the input device 702 with high accuracy when the shape sensor system 308 is static or moves slowly. By using measurement data from different sensor systems (e.g., shape sensor system 308 and local sensor system 704) of different sensing modalities (e.g., shape sensing and IMU) having complementary characteristics, the control system may provide faster and more accurate state estimates of the input device 702, thereby providing improved control of the tool.

The control system may use various techniques to generate state estimates of the input device 702 using measurement data from different sensor systems of different sensing modalities. For example, various filters, including for example, complimentary filter, Kalman filter, particle filter, and other suitable filters, may be applied to the measurement data from the different sensor systems. These techniques may be applied to perform signal processing and filtering of the measurement data from different sensor systems of different sensing modalities, which may reduce noises in the respective suboptimal frequency ranges (e.g., high frequency for the measurement data from the shape sensor system 308, low frequency for the measurement data from the local sensor system 704), which may be complemented by the other sensing modality.

In some embodiments, state estimates of the input device 702 based on measurement data from both the shape sensor system 308 and local sensor system 704 may be used to generate improved shape estimates of the shape sensing fiber of the shape sensor system 308. In subsequent cycles, those improved shape estimates may be used to improve pose measurement data of the distal end 316 of the shape sensor system 308. In some embodiments, the control system may use predetermined shape information (e.g., continuity in shape or change of shape of the shape sensing fiber) associated with specific applications to further improve the estimate accuracy and confidence. In some embodiments, the control system may use shape sensor to compute a first set of the state estimates of the input device (e.g., position, translational velocity, orientation, angular velocity, etc.), while another sensor (e.g., a local sensor) may be used to compute another set of the state estimates of the input device.

Referring to FIG. 8, in some embodiments, an input device is "mechanically grounded" by being connected to a base with a connection structure including a kinematic chain. As illustrated in FIG. 8, in those embodiments, a shape sensor system may be used to determine the configuration (e.g. joint angles) of the kinematic chain (e.g., including a series of articulating links and joints), which is then used for generating state estimates of the input device.

In the example of FIG. 8, an operator input system 800 (e.g., an operator input system 16 of FIGS. 1 and 2) includes an input device 802 (e.g., an operator hand controller 18 of FIG. 2). The input device 802 is connected to a base 304 via a kinematic chain 804. The kinematic chain 804 includes links 806 and 808 connected in a chain by joints 810, 812, and 814. The joints 810, 812, and 814 may be flexure-based joints, mechanical joints, and any other suitable types of joints.

In various embodiments, a shape sensor system 308 may be used to determine the configuration of the kinematic chain 804. As illustrated in FIG. 8, the shape sensor system 308 includes a shape sensing fiber 312 having a proximal end 314 and a distal end 416. The proximal end 314 of the shape sensing fiber 312 is physically (e.g., mechanically) fixed relative to the base 304, and the distal end 316 of the shape sensing fiber 312 is physically fixed relative to the input device 302. The shape sensing fiber 312 may be routed through the kinematic chain 804 in various ways. In some examples, the shape sensing fiber 312 is routed completely internal to the kinematic chain 804, routed completely external to the kinematic chain 804, or routed partially external and partially internal to the kinematic chain 804. In some examples, the shape sensing fiber 312 may be fully constrained on each side of each joint or may slide or float in one or more particular degrees of freedom.

In some embodiments, a control system may determine state estimates of the input device 802 with respect to the base 304 based on the shape information from the shape sensor system 308 and joint information associated with the mechanical structure of each joint. In some examples, the control system may perform a calibration process to estimate the fixed relationships between the shape sensing fiber 312 and reference frames associated with the kinematic chain 804. In some examples, the shape of the shape sensing fiber 312 associated with known link geometries (e.g., a straight link 806) may be used to determine the shape sensing fiber performance (e.g., response, accuracy, and/or other performance properties).

In some embodiments, a control system may determine the configuration of the kinematic chain 804 by using the shape information from the shape sensor system 308 without using any joint data from joint sensors (e.g., encoders, resolvers, potentiometers) of the kinematic chain 804. In those embodiments, the kinematic chain 804 may not include any joint sensors. In alternative embodiments, a control system may determine the configuration of the kinematic chain 804 by using a combination of the shape information from the shape sensor system 308 and joint data from joint sensors of the kinematic chain 804. In an example, the kinematic chain 804 includes joint sensors for joints (e.g., joint 810) located near the proximal (near the base) portion of the kinematic chain 804 that has more space and budget for mass, and does not include joint sensors for joints (e.g., joints 814, 812) located near the distal (near the input device) portion of the kinematic chain 802 that has less space and budget for mass.

By using a shape sensor system 308 to determine the configuration of the kinematic chain 804, which is then used to determine state estimates of the input device, various advantages of various embodiments may be achieved. One advantage of some embodiments is that by eliminating or reducing the number of joint sensors in the kinematic chain 804 and the associated power and communication wirings through the kinematic chain 804, a lighter and more compact input control system is achieved. Another advantage of some embodiments is that the kinematic chain 804 or portion thereof may be disposable or have a limited number of usage. In those embodiments, by using a shape sensor system in the kinematic chain 804 and eliminating or reducing the number of joint sensors, the cost for the kinematic chain 804 is reduced and the sterilizability of the kinematic chain 804 is improved. Yet another advantage of some embodiments is that compared to joint sensors, the shape sensor system may be less sensitive to radio frequency and electromagnetic interference in certain environments (e.g., working close to electrocautery instruments in surgery), which leads to more accurate state estimates of the input device and better control of the tool.

Referring to FIG. 9, in some embodiments, a shape sensor system may be used to determine state estimates (e.g., grip angle, trigger switch state) of subcomponents (e.g., grip levers, trigger switch) of an input device. In the example of FIG. 9, an operator input system 900 (e.g., an operator input system 16 of FIGS. 1 and 2) includes an input device 902 (e.g., an operator hand controller 18 of FIG. 2). The input device 902 includes a pair of grip levers 20 and a trigger switch 22. A control system may control a tool based on the states of the grip levers 20 and trigger switch 22.

In some embodiments, a shape sensor system is used to determine a grip angle of the grip levers of the input device. In the example of FIG. 9, a shape sensor system 904 includes a shape sensing fiber 906 having a proximal end physically fixed relative to a base, and a distal end 908 physically fixed at an end of the grip lever 20 of the input device 902. The shape sensing fiber 906 is routed through the grip levers, and a grip angle 910 may be determined using shape information from the shape sensor system 904.

In some embodiments, the shape sensor system 904 is used to determine a trigger switch state (e.g., on/off) of a trigger switch of the input device. In the example of FIG. 9, the shape sensor system 904 includes a shape sensing fiber 912 having a proximal end physically fixed relative to a base, and a distal end 914 physically fixed at or near the trigger switch 22 of the input device 902. In an example, the shape sensing fiber 912 is routed close to a surface (e.g., a deformable surface) of the trigger switch 22 for contact detection (e.g., based on pressure sensing). In another example, the shape sensing fiber 912 is routed within a button of the trigger switch 22 that bends the shape sensing fiber 912 during actuation (e.g., with a button press or a button slide from an operator). A trigger switch state (e.g., on/off) may be determined based on the shape information provided by the shape sensing fiber 912, and/or inputs from a slider switch that moves the bend location as the switch slides.

In some embodiments, the shape sensor system 904 uses the same shape sensing fiber(s) (e.g., shape sensing fiber 906 or 912 or a combination thereof) used to determine the grip angle of the grip levers of the input device and/or trigger switch state to also provide measurement data of the pose of the input device 902. In alternative embodiments, the shape sensor system 904 uses a separate shape sensing fiber for the shape sensing fiber 906 or 912 to provide measurement data of the pose of the input device 902.

Referring to FIG. 10, illustrated therein is a method 1000 for controlling a tool using an input device according to an embodiment of the present disclosure. Method 1000 is described in connection with a teleoperational medical system controlling a medical tool using the input device. However, the technique illustrated by method 1000 may also be used in connection with other medical systems with other medical tools or non-medical systems with non-medical tools. The method 1000 is illustrated in FIG. 10 as a set of operations or processes 1002 through 1012. Not all of the illustrated processes 1002 through 1012 may be performed in all embodiments of method 1000. Additionally, one or more processes that are not expressly illustrated in FIG. 10 may be included before, after, in between, or as part of the processes 1002 through 1012. In some embodiments, one or more of the processes may be implemented, at least in part, in the form of executable code stored on non-transitory, tangible, machine-readable media that when run by one or more processors (e.g., the processors of control system) may cause the one or more processors to perform one or more of the processes.

At a process 1002, an input device in a teleoperational medical system for controlling a tool is provided. The input device is connected to a base via a connection structure which includes a shape sensor system. In the example of FIG. 3, an input device 302 is connected to a base 304 via a connection structure 306 (e.g., a flexible body), which includes a shape sensor system 308. In the example of FIG. 4, an input device 302 including hand controllers 402 and 404 is connected to a base 304 via a connection structure 306 (e.g., a flexible body), which includes a shape sensor system 406. In the example of FIG. 5, an input device 502 is connected to a base 304 via a connection structure 306 (e.g., a flexible body), which includes a shape sensor system 504. In the example of FIG. 6, an input device 602 is connected to a base 304 via a connection structure 306 (e.g., a flexible body), which includes a shape sensor system 604. In the example of FIG. 7, an input device 702 is connected to a base 304 via a connection structure 306 (e.g., a flexible body), which includes a shape sensor system 308. In the example of FIG. 8, an input device 802 is connected to a base 304 via a connection structure 804 (e.g., a kinematic chain), which includes a shape sensor system 308.

At a process 1004, a control system (e.g., control system 28 of FIG. 1) receives shape information associated with the connection structure and the input device from the shape sensor system. In some examples, an interrogator system (e.g., interrogator system 310 of FIGS. 3-8) may be used to generate the shape information from the shape sensor system.

At a process 1006, the control system receives, from a local sensor system located at the input device, local measurement data of the input device. In the example of FIG. 7, the control system may receive, from a local sensor system 704 at the input device 702, local measurement data of the input device 702.

At a process 1008, the control system determines state estimates (e.g., pose estimates, motion estimates) of the input device based on the shape information from the shape sensor system, the local measurement data from the local sensor system, and/or a combination thereof. In the example of FIG. 7, the control system may generate state estimates of the input device 702 based on the shape information from the shape sensor system 308, the local measurement data from the local sensor system 704, and/or a combination thereof. Various filters (e.g., complimentary filter, Kalman filter, particle filter, and other suitable filters) may be applied to the shape information from the shape sensor system and the local measurement data from the local sensor system. In some examples, the control system may generate state estimates of the input device 702 by generating low frequency state estimates of the input device based on the shape information from the shape sensor system 308, and generating high frequency state estimates of the input device 702 based on the local measurement data from the local sensor system 704.

At a process 1010, the control system determines subcomponent state estimates (e.g., grip angle, switch state) of subcomponents of the input device based on the shape information from the shape sensor system. In the example of FIG. 9, the control system may determine a subcomponent state estimate of a grip angle 910 of the grip levers 20 based on the shape information from a shape sensing fiber 906 of the shape sensor system 904. The control system may also determine a subcomponent state estimate of a switch 22 based on the shape information from a shape sensing fiber 912 of the shape sensor system 904.

At a process 1012, the control system controls a tool (e.g. tool 14), using a manipulator (e.g., an arm of the teleoperational assembly 13) based on the state estimates and subcomponent state estimates of the input device.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor-readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read-only memory (ROM), a flash memory, an erasable programmable read-only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
    a tool coupled to a tele-operational manipulator;
    an input device for tele-operationally controlling the tool, wherein the input device is connected to a base via a kinematic chain;
    a connection structure connecting the input device for tele-operationally controlling the tool and a base, wherein a shape sensor system is configured to provide shape information of the connection structure, wherein a distal end of the shape sensor system and a location of a local sensor system located at the input device are physically fixed with respect to one another; and
    a processing unit configured to:
        calibrate a fixed transformation between a shape sensor termination frame fixed to the distal end of the shape sensor system and a local sensor frame of reference;
        determine a configuration of the kinematic chain based on the shape information from the shape sensor system;

determine a state estimate of a state of the input device based on shape information from the shape sensor system, local measurement data of the input device from the local sensor system, and the configuration of the kinematic chain,
  wherein the state includes a motion state including one or more of a velocity and an acceleration of the input device; and
control, using the tele-operational manipulator, the tool based on the state estimate of the input device.

2. The system of claim 1, where the system further comprises:
an interrogator system configured to sense strain information associated with the shape sensor system;
wherein the processing unit is configured to:
  receive, from the interrogator system, the strain information; and
  determine the shape information based on the strain information.

3. The system of claim 1,
wherein the shape sensor system includes a shape sensing fiber having a first portion physically fixed relative to the base and a second portion physically fixed relative to the input device.

4. The system of claim 1, wherein the input device includes:
a first hand controller configured to be moved by a first hand of an operator; and
a second hand controller configured to be moved by a second hand of the operator;
wherein the shape sensor system includes a shape sensing fiber routed through the first hand controller and second hand controller.

5. The system of claim 1, wherein the processing unit is configured to:
determine the shape information associated with the shape sensor system by combining first shape information from a first shape sensing fiber and second shape information from a second shape sensing fiber.

6. The system of claim 1, wherein the input device includes:
a hand controller including a body and one or more grip levers coupled to the body, wherein the one or more grip levers are configured to be gripped by a hand of an operator;
wherein the shape sensor system includes a first shape sensing fiber and a separate second shape sensing fiber routed through a first grip lever of the input device;
wherein the first shape sensing fiber has a proximal end physically fixed relative to a base, and a distal end physically fixed at an end of a grip lever of the input device;
wherein the second shape sensing fiber is routed close to a surface of a trigger switch of the input device,
wherein the processing unit is configured to:
  estimate a grip angle associated with the one or more grip levers using the shape information; and
  control the tool based on the grip angle estimate.

7. A method, comprising:
receiving shape information from a shape sensor system, wherein the shape sensor system is associated with a connection structure connecting an input device for tele-operationally controlling a tool and a base;
wherein the input device is connected to a base via a kinematic chain;
  wherein a distal end of the shape sensor system and a location of a local sensor system located at the input device are physically fixed with respect to one another;
  wherein the tool is coupled to a tele-operational manipulator;
calibrating a fixed transformation between a shape sensor termination frame fixed to the distal end of the shape sensor system and a local sensor frame of reference;
determining a configuration of the kinematic chain based on the shape information from the shape sensor system;
determining a state estimate of a state of the input device based on the shape information, local measurement data of the input device from the local sensor system, and the configuration of the kinematic chain,
  wherein the state includes a motion state including one or more of a velocity and an acceleration of the input device; and
controlling, using the tele-operational manipulator, the tool based on the state estimate of the input device.

8. The method of claim 7, further comprising:
receiving strain information associated with the shape sensor system, from an interrogator system coupled to the shape sensor system; and
determining the shape information based on the strain information.

9. The method of claim 7, further comprising:
providing the shape information using a shape sensing fiber of the shape sensor system, the shape sensing fiber having a first portion physically fixed relative to the base and a second portion physically fixed relative to the input device.

10. The method of claim 7, wherein the input device includes:
providing the shape information using a shape sensing fiber of the shape sensor system, wherein the shape sensing fiber is routed through a first hand controller of the input device and a second hand controller of the input device,
wherein the first hand controller is configured to be moved by a first hand of an operator; and
wherein the second hand controller is configured to be moved by a second hand of the operator.

11. The method of claim 7, further comprising:
determining the shape information by combining first shape information from a first shape sensing fiber and second shape information from a second shape sensing fiber.

12. The method of claim 7, further comprising:
estimating a grip angle associated with one or more grip levers of the input device using the shape information; and
controlling the tool based on the grip angle estimate.

13. A non-transitory machine-readable medium comprising a plurality of machine-readable instructions which, when executed by one or more processors, are adapted to cause the one or more processors to perform a method comprising:
receiving shape information from a shape sensor system associated with a connection structure connecting an input device for tele-operationally controlling a tool and a base,
  wherein the input device is for tele-operationally controlling a tool;
  wherein a distal end of the shape sensor system and a location of the local sensor system are physically fixed with respect to one another;

wherein the tool is coupled to a tele-operational manipulator;

calibrating a fixed transformation between a shape sensor termination frame fixed to the distal end of the shape sensor system and a local sensor frame of reference;

determining a configuration of the kinematic chain based on the shape information from the shape sensor system;

determining a state estimate of a state of the input device based on the shape information, local measurement data of the input device from the local sensor system, and the configuration of the kinematic chain, wherein the state includes a motion state including one or more of a velocity and an acceleration of the input device; and controlling, using the tele-operational manipulator, the tool based on the state estimate of the input device.

14. The non-transitory machine-readable medium of claim 13, wherein the method further comprises:

receiving strain information associated with the shape sensor system, from an interrogator system coupled to the shape sensor system; and determining the shape information based on the strain information.

15. The non-transitory machine-readable medium of claim 13, wherein the method further comprises:

providing the shape information using a shape sensing fiber of the shape sensor system, the shape sensing fiber having a first portion physically fixed relative to the base and a second portion physically fixed relative to the input device.

16. The non-transitory machine-readable medium of claim 13, wherein the input device includes:

providing the shape information using a shape sensing fiber of the shape sensor system, wherein the shape sensing fiber is routed through a first hand controller of the input device and a second hand controller of the input device, wherein the first hand controller is configured to be moved by a first hand of an operator; and wherein the second hand controller is configured to be moved by a second hand of the operator.

17. The non-transitory machine-readable medium of claim 13, wherein the method further comprises:

determining the shape information by combining first shape information from a first shape sensing fiber and second shape information from a second shape sensing fiber.

18. The non-transitory machine-readable medium of claim 13, wherein the method further comprises:

estimating a grip angle associated with one or more grip levers of the input device using the shape information; and controlling the tool based on the grip angle estimate.

* * * * *